United States Patent
Goel et al.

(10) Patent No.: US 11,127,306 B2
(45) Date of Patent: Sep. 21, 2021

(54) MEDICAL VIRTUAL REALITY SURGICAL SYSTEM

(71) Applicant: Precisionos Technology Inc., Vancouver (CA)

(72) Inventors: Danny P. Goel, North Vancouver (CA); Roberto Oliveira, North Vancouver (CA); Colin O'Connor, Vancouver (CA)

(73) Assignee: Precisionos Technology Inc., Vancouver (CA)

( * ) Notice: Subject to any disclaimer, the term of this patent is extended or adjusted under 35 U.S.C. 154(b) by 0 days.

(21) Appl. No.: 16/072,490

(22) PCT Filed: Aug. 21, 2017

(86) PCT No.: PCT/CA2017/050990
§ 371 (c)(1),
(2) Date: Jun. 3, 2019

(87) PCT Pub. No.: WO2019/036790
PCT Pub. Date: Feb. 28, 2019

(65) Prior Publication Data
US 2019/0318640 A1  Oct. 17, 2019

(51) Int. Cl.
*G09B 5/02* (2006.01)
*G09B 23/30* (2006.01)
(Continued)

(52) U.S. Cl.
CPC ............... *G09B 5/02* (2013.01); *A61B 34/10* (2016.02); *G06F 3/012* (2013.01); *G06F 3/013* (2013.01);
(Continued)

(58) Field of Classification Search
None
See application file for complete search history.

(56) References Cited

U.S. PATENT DOCUMENTS

2003/0191466 A1* 10/2003 Austin ................... A61B 17/62
606/54
2010/0311028 A1* 12/2010 Bell, III ................ G09B 23/28
434/263
(Continued)

FOREIGN PATENT DOCUMENTS

WO    WO 2000/53007 A1    9/2000
WO    WO 2014/151585 A1   9/2014

OTHER PUBLICATIONS

International Search Report and Written Opinion for PCT/CA2017/050990, dated Apr. 30, 2018, 10 pages.

*Primary Examiner* — Michelle Chin
(74) *Attorney, Agent, or Firm* — Klarquist Sparkman, LLP

(57) ABSTRACT

A virtual reality system for simulating medical processes is described, which may include a variety of features and functions, and may implement a variety of processes. In a typical illustrative situation, the virtual reality system supports a system in which a virtual medical procedure may be performed on a virtual patient (or a part thereof), the virtual patient having medical conditions that simulate those of an actual real-world patient. The virtual reality system enables a user, such as a physician, to develop a strategy for treating the actual patient by performing one or more procedures on a simulated virtual patient.

7 Claims, 14 Drawing Sheets

(51) Int. Cl.
  *G06F 3/01*      (2006.01)
  *G06T 19/00*     (2011.01)
  *A61B 34/10*     (2016.01)
  *A61B 90/00*     (2016.01)
  *A61B 90/50*     (2016.01)
  *G09B 5/06*      (2006.01)

(52) U.S. Cl.
  CPC .............. *G06F 3/014* (2013.01); *G06F 3/016* (2013.01); *G06T 19/006* (2013.01); *G09B 23/30* (2013.01); *A61B 2034/104* (2016.02); *A61B 2034/105* (2016.02); *A61B 2090/365* (2016.02); *A61B 2090/502* (2016.02); *G09B 5/06* (2013.01)

(56) References Cited

U.S. PATENT DOCUMENTS

| | | | |
|---|---|---|---|
| 2014/0272863 A1* | 9/2014 | Kim | G06T 19/006 434/262 |
| 2017/0108930 A1* | 4/2017 | Banerjee | A61B 90/37 |
| 2017/0196499 A1* | 7/2017 | Hunter | A61B 5/066 |
| 2017/0258526 A1* | 9/2017 | Lang | A61F 2/32 |

* cited by examiner

MEDICAL VIRTUAL REALITY SURGICAL SYSTEM

CROSS REFERENCE TO RELATED APPLICATIONS

This is the U.S. National Stage of International Application No. PCT/CA2017/050990, filed Aug. 21, 2017, which was published in English under PCT Article 21(2).

TECHNICAL FIELD

This disclosure relates generally to processes and apparatus for computer processing involving input and output that may be any combination of visual/graphics, audible, tactile/haptic, spatial, virtual reality, mixed reality, and/or augmented reality; and more particularly, to such processes and apparatus involve manipulation of data representing medical objects such as anatomical structures, medical instruments and other medical devices, prosthetics, and implants.

BACKGROUND

The art and science of Medicine has a rich and lengthy history. Some surgical training has come in the form of operations upon cadavers (whole or parts of dead bodies). Apart from the economic considerations pertaining to acquiring and keeping cadavers, a cadaver might be physically different from a particular patient. Many traditional methods of medical practice have tended to focus upon in-person examination of a living patient. A physician may examine the patient, and request that various examinations be performed and images be captured. Using this data, and perhaps consulting with local physicians, the physician will determine an approach for treating the patient, implement the approach, and observe how the patient responds to the treatment that the patient has received.

DETAILED DESCRIPTION

Figure 1:
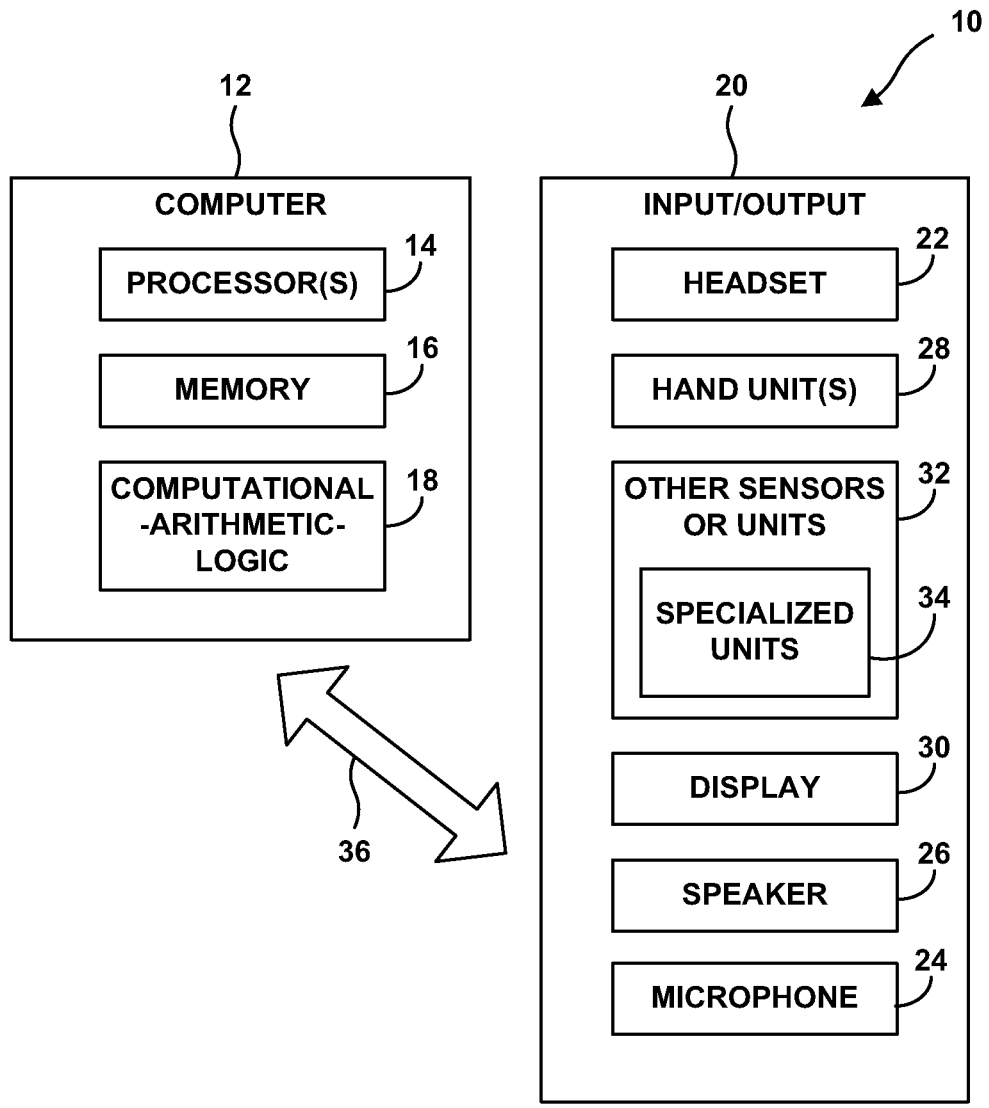
FIG. 1 is a schematic diagram of an illustrative virtual reality platform that may realize one or more embodiments of the concepts described herein.

This concept described herein is directed toward apparatus and methods pertaining to medical processes. The methods may be implemented by, for example, hardware, software, firmware, or any combination thereof. The apparatus may be configured to carry out the methods. As used herein, an object is "configured to" do a thing when the object is adapted to do the thing or is made to do the thing or is capable of doing the thing or is arranged to do the thing. A processor configured to perform a part of a method, may be so configured through execution of software instructions, for example.

The art and science of Medicine is forever striving to improve. Medicine has a history of drawing upon long-used and time-tested techniques, as well as new techniques that may supplement or supplant the older techniques. For purposes of the discussion that follows, the concepts to be described here will be described in the context of Orthopedics. Orthopedics is generally the branch of Medicine concerned with the human musculoskeletal system, and encompasses a variety of medical disciplines including diagnosing and treating (surgically or non-surgically) various conditions, traumas, injuries diseases, and other disorders. The concepts described herein are not necessarily limited to Orthopedics, however (though one or more claims may be), but may be adapted to a variety of uses in Medicine such as craniofacial surgery, or any bone, soft tissue injury or tear, or other surgical and non-surgical specialties. Dentistry, and Veterinary practice may also be included, as may patient education and rehabilitation.

Medical practice (the word "practice" being used in this sentence to connote a repeated exercise of an activity or skill so as to acquire or maintain proficiency in or improve the activity or skill) may benefit from the use of virtual reality. Generally speaking, virtual reality involves the use of a simulation rather than a living patient or tangible objects. In virtual reality, the simulation may be achieved with a computer, which may render a three-dimensional image of an object (such as a medical instrument, or apparatus, or a patient, or a part of a patient), or an environment (such as a clinic or an operating room), or any combination thereof. A user experiencing virtual reality may interact with the simulated objects or environments, in a manner that may simulate reality. The interaction is typically enabled by virtual reality equipment, which will be described in more detail below.

Medical practice (the word "practice" being used here to connote the carrying out or exercise of a profession, usually including the customary or expected procedures of the profession) may also benefit from the use of virtual reality.

In this disclosure, the term "virtual reality" will encompass a variety of computer-aided simulations. In some contexts, "virtual reality" may encompass augmented reality and some further variations.

There are many platforms that support virtual reality. A platform may be thought of as hardware and software and other apparatus that support generation of virtual reality simulations. Some commercially available platforms for virtual reality include various gaming systems, in which a user interacts with a simulated environment and objects in that environment. Some platforms support a variety of simulations; others are more specialized. Some platforms support customization by granting a developer access to code, objects, procedures, assets, files, and other tools for building a simulation; other platforms are less susceptible to customization. The concepts described here are not restricted to any particular virtual reality platform.

FIG. 1 is a representation of a typical virtual platform 10. Not all platforms include all of these elements, and some platforms include more elements than are depicted. A computer 12 generates the simulated objects and environment. A typical computer 12 may include one or more processors 14, memory 16, and subsidiary processing units 18 that perform certain arithmetic or logical operations. Virtual elements exist in the real word as representations within the computer 12, processors 14, memory 16, and subsidiary processing units 18. Memory 16 may include volatile and non-volatile memory of any kind, stored in any fashion on any hardware (including cloud storage). Memory 16 may store software, which may comprise instructions and data that, when executed or used, enable the computer 10 to realize the simulation. The simulation may be realized through a combination of hardware and software. Specialized hardware or software (or combinations thereof) may operate with the platform 10 to realize a more specific simulation, such as a simulation involving specific objects or specific environments or specific interactions.

Although depicted in FIG. 1 as a single unit, the computer 12 may be realized as a series of separate or distributed units communicatively connected by a communications network. It is not necessary that all components of the computer 12 be located in proximity to one another, or in proximity to any user.

The virtual reality platform 10 supports user interaction with the simulation through one or more input/output devices 20. Some of the input/output devices 20 may receive input from a user but generate no output to a user; some may generate output to a user but receive no input from a user, and some may receive input from a user and generate output to a user.

In FIG. 1, most of the processing that generates the simulation may performed by the computer 12. In some variations of the concept, processing (or portions of the processing) may be performed by the input-output devices 20 as well.

A typical input-output device is a headset 22. A headset 22 is an input-output device 20 that receives input from a user and generates output to a user. By wearing a headset 22, a user may more fully experience the simulation. Some headsets 22 may cover the user's eyes, and others may cover the user's eyes and ears. The input received by the headset 22 may include positional sensors that respond to movements and/or orientation of the head of a user wearing the headset 22. A headset 22 may include positional sensors that respond to movements of the head of a user in space (in some cases, such positional sensors are physically set apart from the headset 22). Some headsets 22 may also include sensors (not shown in FIG. 1) that monitor the eyes of the user, and respond to the direction in which the user happens to be looking. Some headsets may include sensors (not shown in FIG. 1) that monitor facial expressions of a user, or whether the user is speaking. Some headsets 22 may include a microphone (on some platforms, the microphone 24 may be a distinct element, not incorporated in the headset 22) that receives input in the form of audio. Various headsets 22 may include other sensors as well (not shown in FIG. 1), responding to any number of factors, such as touch, pressure, temperature, or user physiology.

A headset 22 generates output. Typically the headset 22 generates moving-picture output (or video output) that can be seen by a user. Often the visual output is presented to a user with one point of view for a right eye and a different point of view for a left eye, allowing the user to perceive the video output in three dimensions. Some headsets 22 may include one or more speakers (on some platforms, the speaker 26 may be a distinct element). Some headsets 22 may include haptic feedback elements (not shown in FIG. 1), which generate output that can be detected by touch, such as vibration or pressure or shifting weights or moving parts or other tactile activity, or any combination thereof.

The concepts described herein are not limited to any particular kind of headset 22.

Another typical input-output device is a hand unit 28. The hand unit 28 may be of any of several configurations. The hand unit 28 in some embodiments may be a handheld game controller used with virtual reality games. In other embodiments, the hand unit 28 may be a complete or partial glove-like unit that a user may wear on the hand. In further embodiments, the hand unit may be a simulated medical instrument, such as (but not limited to) a simulated saw or drill. A hand unit 28 may be of other configurations as well, and may include any combination of the kinds of hand units mentioned specifically.

Some virtual reality platforms 10 support hand units 28 for more than one hand. The input received by the hand unit 28 may include positional sensors that respond to movements of the hand of a user in space (in some cases, such positional sensors are physically set apart from the hand unit 28). Positional sensors may also respond to the position of the parts of the hand, such as the positions of the fingers or thumb. Various hand units may include other sensors as well. A typical hand unit 28 further supplies haptic output, such as has already been mentioned.

A typical hand unit 28 receives an input from a user, in forms such as movement, location, activation of a device, and so forth. The processor 14 generally receives this input from the hand unit 28. The processor 14 may receive this input as transduced by the hand unit 28, for example, converting the movement of the hand unit 28 by the user into a signal that encodes the movement.

Additional input-output devices, such as a separate display 30, or a speaker 26, or a microphone 24, may also be a part of the virtual reality platform. A separate display 30 may be included so that someone other than the user may experience part of the simulation being experienced by the user. Some platforms may include additional sensors or units 32, such as units worn on the legs, or sensors that respond to the position of the user's body as a whole. In some embodiments, the additional sensors 32 may be deployed away from the other input-output devices 20, to detect the location of such devices in space, for example.

Though the concepts will be described in connection a virtual reality platform that supports a headset 22 and at least one hand unit 28 (and usually two hand units, one for the user's right hand and one for the user's left hand), it is contemplated that the concepts may applied to more expansive virtual reality platforms.

Also, it is contemplated that some of the additional sensors or units 34 may be specific to a particular simulation or a particular type of simulation. For example, an input-output device 20 may include a simulated (yet tangible) medical instrument (or other device) that may be picked up or handled or otherwise manipulated by a user. The simulated medical instrument may include positional sensors that respond to movements of the simulated medical instrument in space or orientation, and may include one or more output elements such as an element that provides haptic output. In addition, the simulated medical instrument, by its physical shape or weight or other characteristics, may supply feedback to the user, in that the user may experience a weight or torque or other physical effect that can be detected by the user.

All of the components of the virtual reality platform 10 may communicate with one or more components of the platform. A generic communication pathways 36 depicted in FIG. 1 may be realized in any number of ways, some of them quite complicated. In some embodiments, the computer 12, or some components thereof, need not be physically proximate to the input-output elements 20. The computer 12 and the input-output elements 22 may communicate electronically directly or through one or more intermediate elements, such as a network. The network may be a large network, such as the Internet, or a small network, or a combination of networks. Communications may be by conductive pathway (such as electrically conductive wire or fiber optic connection) or by any wireless pathway, or any combination thereof. Further, any form of communication pathway may be used for components of the computer 12 to communicate among one another, or for input-output devices 20 to communicate among one another. The concepts described herein generally do not require any particular path or paths of communication.

When in operation, the virtual reality platform 10 enables a user to see, feel, touch, manipulate, hear, move around, and generally interact with the simulated environment and objects therein. In some ways, a simulation that more accurately resembles the real world may be regarded as a better simulation; but may also be the case that a simulation may offer experiences that have no counterpart in the real world. As will be discussed below, some implementations and features may involve making the simulation seem very real to a user (such as use of realistic virtual medical devices and operating on virtual bones that look like the real bones of a patient); while other implementations may involve features that have little or no real-world equivalent (such as an opportunity to do over a virtual operation that did not go well).

In the concepts described in more detail below, the simulation includes medical data, such as patient-specific data about a bone of a particular patient. The patient-specific data may be used to generate a virtual bone, which is a representation of a corresponding bone, such as facial bones, spin, pelvic, upper and lower extremities, in the actual body of the patient. The virtual reality simulation may enable the user (among other things) to see the virtual bone, to reorient the virtual bone so that the virtual bone may be seen from any desired point of view, to observe any feature or condition of the virtual bone (such as a fracture), to manipulate the virtual bone, and to virtually treat or repair the virtual bone (such as by cutting, bracing, screwing, re-fitting, administering an injection near, removing/amputating, or manipulating tissue proximate to the virtual bone). In aspects, the virtual reality simulation can include all aspects of orthopedic surgery, including specialties such as trauma, spine, should and elbow, hand and wrist, and joint replacements (arthroplasty) for all joints including the shoulder, elbow, wrist, hand, hip, knee, ankle and foot). Further, the simulation supports assessment of the virtual treatment or repair; and enables one or more different modes of treatment or repair to be simulated and assessed, as will be described in more detail below. In this way, a user may evaluate what form of treatment or repair would be more likely to be a better strategy for a particular patient.

Such a simulation need not be limited to a single bone (or virtual bone). A simulation may take into account other structures such as muscles, organs, circulatory vessels, nerves, ligaments, tendons, or connecting tissue; a simulation may take into account multiple bones, such as a simulation depicting a fracture of a radius and neighbouring ulna; a simulation may take into account a multi-bone structure involving bones and other tissues, such as a spine and its intervertebral disks, or a craniofacial structure involving the skull and tissues of the head and face.

Figure 2:
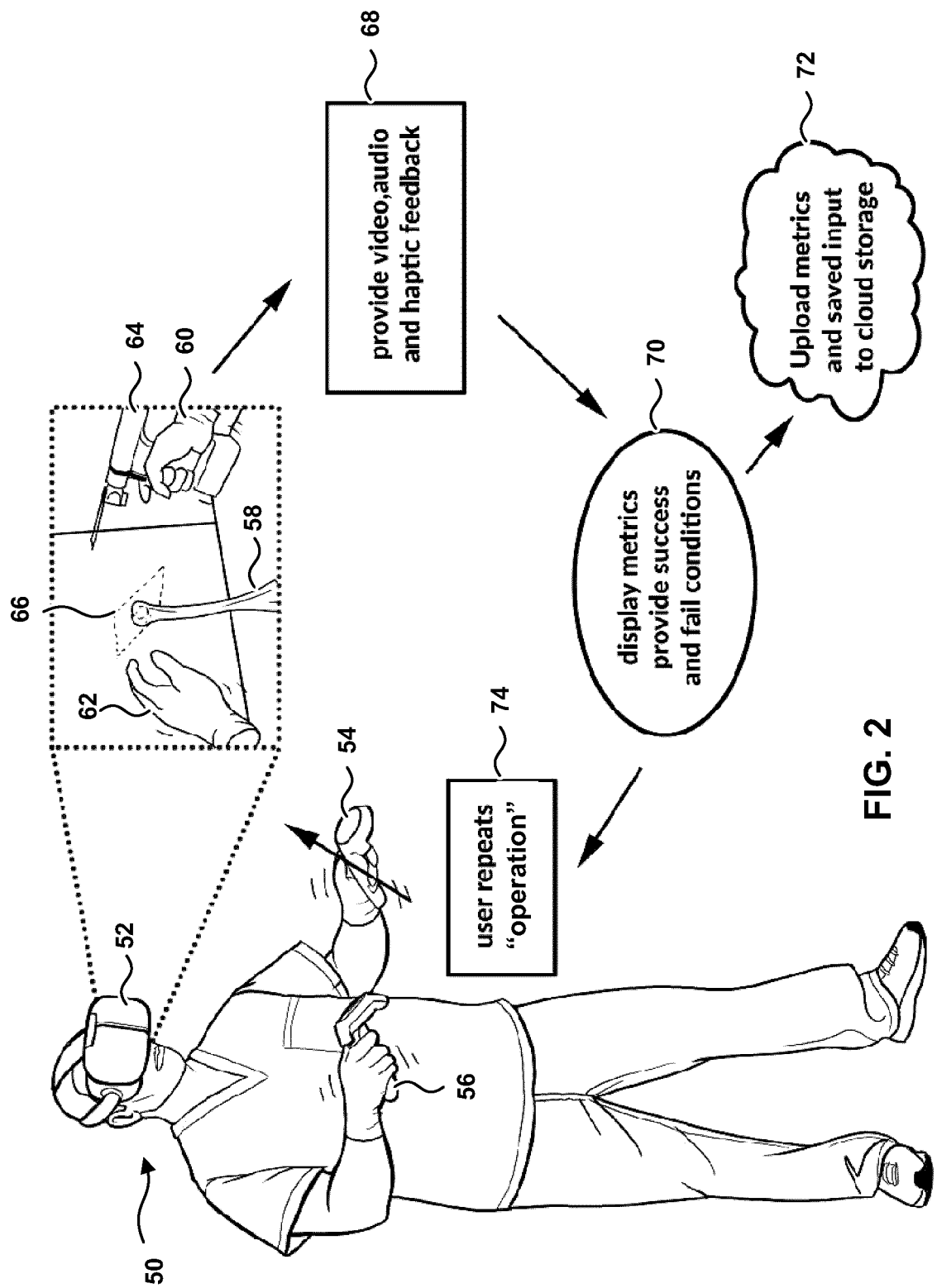
FIG. 2 is a combination visual representation of a virtual reality illustration, and a flow diagram illustrating a typical embodiment of the concepts.

The overall application of the concept to an illustrative orthopedic situation is depicted in FIG. 2. As shown in FIG. 2, a user 50 is equipped with an illustrative headset 52 and two hand units 54, 56 (depicted in FIG. 2 as generic controllers, such as game controllers). By way of the headset 52, the user can see a virtual bone 58. The virtual bone 58 may be very similar in size and condition to the particular bone of a particular patient (the virtual bone 58 being based upon one or more actual medical scans of the particular patient, such as a computerized tomography (CT) scan), or it may be an "average" bone of a "typical" or "idealized" patient. In FIG. 2, the virtual bone 58 is depicted as disembodied, that is, separate and distinct from the patient as a whole. Some of the concepts herein may be applied to a virtual patient, that is, a simulation of a patient in which the body parts are not depicted as disembodied.

By way of the headset 52, the user 50 can also see the virtual right hand 60 of the user, and the virtual left hand 62 of the user. In the real world, the actual left hand of the user holds a controller 54; but in the virtual world, the virtual left hand 62 is empty. The controller enables the virtual reality simulation to place a representation of the user's left hand 62 into the simulation in a proper position and orientation. The controller 54 may also supply haptic output to the user's left hand in response to a haptic output generated by the processor 14.

The actual right hand of the user holds a separate controller 56, but the virtual right hand 60 holds a virtual medical device or instrument 64. The controller 56 enables the virtual reality simulation to place a representation of the user's right hand 60 into the simulation in a proper position and orientation, and to supply haptic output to the user's right hand. The controller 56 may further include one or more physical controls (such as a trigger) that, when activated or deactivated by the user 50, may cause the virtual medical device 64 to become activated or deactivated in the simulation. The user 50, by manipulating physical controls on the controller 56, may, for example, turn on the virtual medical device 64, turn off the virtual medical device 64, or control the speed of the virtual medical device 64.

As already noted, one or more controllers 54, 56 may be specially designed, constructed, shaped, weighted or otherwise configured to physically resemble medical instruments.

With the right hand or the left hand or both of the user 50, the user 50 may activate one or more controllers 54, 56 to virtually take hold of the virtual bone 58 and virtually move the virtual bone 58 in any desired fashion in three dimensions. In this way, the user can examine the virtual bone 58 from a desired point of view, and can examine any feature or condition of the virtual bone 58. In some embodiments, a virtual hand 60, 62 may take hold of the virtual bone 58 itself; in other embodiments, the virtual hand 60, 62 may manipulate the virtual bone 58 by manipulating a virtual frame or handle 66. In some embodiments, the virtual frame 66 may serve as an anatomical guide for performing a procedure, such as making a cut.

Further, with the right hand or the left hand or both of the user 50, the user 50 may activate one or more controllers 54, 56 to virtually treat or repair the virtual bone 58.

In response to the movement by the user 50 of the controllers 54, 56, and in response to the activation of the controllers 54, 56 by the user 50, the simulation may generate one or more outputs 68. Video output may show the position and orientation of the virtual bone 58, and the positions and orientations of the virtual hands 60, 62 in relation to the virtual bone 58. Video output may further show changes to the virtual bone 58 resulting from the virtual treatment or repair. As will be discussed below, video output may also include a visual representation of a virtual construct that has no physical counterpart in the real world, such as a target cylinder. Audio output may indicate any sort of sound information, such as a noise simulation of an activated virtual medical instrument 64, or an auditory indication of a position or orientation of something else in the simulation, or a voice of a simulated assistant, or an alarm indicating a hazardous condition. Haptic output may supply tactile feedback to the user, such as through the controllers 54 and/or 56, indicating any touch-related information, such as a simulation of vibrations caused by an activated virtual medical instrument 64, or resistance of a virtual bone 58 (or part thereof) to movement or manipulation, or acknowledgment that the virtual bone 58 is being held by a virtual hand 60 and/or 62, or indicating a hazardous condition.

Also, with the right hand or the left hand or both of the user 50, the user 50 may activate one or more controllers 54, 56 to select a virtual medical device that is incapable of being activated. Such medical devices may include, for example, braces or screws or adhesives or pins, for example. The user 50 may be presented with an array of medical devices (whether capable of activation or not) in any fashion, such as a menu or an array of virtual devices laid out on a virtual table.

As a general matter, it is up to the judgment of the user 50 to make an assessment of the virtual bone 58 and any features or conditions of the virtual bone 58. It is further left to the judgment of the user 50 any method or methods for virtually treating or repairing the virtual bone 58. (In some embodiments, the simulation may offer suggestions or options for different ways of treating or repairing the virtual bone 58; the decision of as to which option to try is up to the user 50.) For purposes of illustration, the user 50 may be presented with a specific virtual bone 58 having a specific (or patient-specific) condition, such as a virtual humerus having a spiral fracture. It may be up to the user 50 to evaluate the seriousness of the fracture and the method for virtually treating the spiral fracture.

In many cases, different users may assess the same conditions (whether in a simulation or in a real-life patient) differently, and may judge different treatments or repairs as most likely to be the most promising strategies. In the concepts described here, the user 50 may, by way of simulation, try one particular method for treatment or repair, and then try a different method of treatment or repair, and compare the outcomes, or compare and contrast the differences and challenges that may come with different strategies. The user 50 may, by trying different approaches and assessing the outcomes of each approach, obtain knowledge as to which of several approaches may be more likely to produce a better strategy for a particular patient.

The simulation can assist in the user 50 in assessment of various outcomes of a chosen approach, by generating and presenting one or more metrics 70 indicative of success or failure (or indicative of outcomes that are more desirable or less desirable). In general, a typical metric may be generated as a result of a comparison of the virtual outcome to a standard (typically a pre-defined standard, that is, a standard defined prior to generation of the metric and that may be defined prior to the virtual procedure or prior to the execution of the virtual reality simulation). A standard may be, for example, an ideal outcome, or a generalized outcome typical of similar bones having similar conditions, or some other possible outcome. Comparison may be by, for example, analysis of primitive shapes that make up the virtual bone 58 and the comparison bone, or by vector analysis of the positions or movements of the virtual bone 58 with respect to the comparison bone, or by mathematical correlation of measurements of the virtual bone 58 with respect to the comparison bone, or by any other comparison technique or combination of comparison techniques.

Such metrics may include any of the following: the degree of physical matching between the repaired virtual bone 58 and an idealized virtual bone (e.g., by comparing the relative positions of various bone landmarks in three-dimensional space); the alignment of the repaired virtual bone 58 in comparison to an alignment that would be exhibited by an idealized virtual bone; the estimated ability of the repaired virtual bone 58 to resist injury (or deformation) in response to external conditions such as stresses, strains or impacts; the degree of removal of material or patient trauma to achieve the virtual repair or the estimated time of patient recovery; the estimated loss of use or disability that may be associated with such a virtual repair; the risk of re-injury or other complication associated with the virtual repair; or the prospects of further or follow-up procedures (such as a follow-up procedure to surgically remove an implanted brace).

The metrics may be presented to a user 50 in any fashion, using any combination of visual, auditory, or haptic output. Typical metrics may be presented to the user 50 visually by way of the headset 52. Metrics may be presented as, for example, tabulated numerical data, or written textual results, or graphical depictions, or any combination thereof. Any units—such as degrees, radians, millimeters, centimeters, grams, pounds—may be included as part of a presented metric.

The actions taken by the user 50 to repair or treat the virtual bone 58, and the results of the repair or treatment, and the metrics generated in response to the repair or treatment, may be stored in memory 72 for later review. As shown in FIG. 2, this information may be stored in cloud storage, for example.

After assessing the outcomes of a particular treatment or repair on a particular virtual bone, the user 50 may choose to repeat the treatment or repair 74, using a different approach. In such a situation, the simulation may reset to an initial state, in which the virtual bone 58 appears as if no treatment or repair has been performed. The user 50 may try a different approach (which may be but need not be significantly different from a previous approach), which may generate a different (perhaps better in some ways, perhaps worse in some ways, perhaps indifferent) outcome, and different metrics.

By comparing the fixation methods and locations of various approaches as applied to a virtual bone 58, a user 50 may determine which approach or strategy may be deemed most likely to be better or best for a real-life patient that has the real-world bone that is the basis for the virtual bone 58.

By comparing the fixation methods and locations of various approaches as applied to a virtual bone 58, a user 50 may also determine which approach or strategy may be deemed better for a patient having a bone with a condition similar to the condition of the virtual bone 58. A user 50 may also be able to rule out approaches that seem to have serious practical problems or that yield unsatisfactory results.

In an embodiment, the stored data (user actions or inputs, video, audio, haptic, metrics) may be stored separately for each patient. In another embodiment, the data for multiple patients may be stored in the form of a searchable library. (It may be assumed that, though the data may be patient-specific, all identifying information about a patient may be scrubbed or encrypted or otherwise protected, so as to preserve patient confidentiality.) The searchable library may include data based upon a plurality of patients. A user, presented with a particular patient, may search the library to see how patients having a similar condition were treated, and what kinds of results might be expected. The library may contain results of virtual procedures as well as real life procedures.

A user (such as an orthopedic surgeon), presented with an uncommon form of spiral fracture in the humerus of a patient, for example, may search the library to determine whether other patients have been seen having similar spiral fractures, and what virtual and actual approaches have been tried, and the results of such approaches. In this way, a user may identify which approaches are more likely to yield favourable results. A user may also gather data for research purposes, or learning from the experience of a remote expert (such as a remote orthopedic surgeon). Such retrieved data may be presented in conventional fashion (such as on a conventional display), or may be presented in the form of a virtual reality simulation (in which the user's interaction with the simulation may be more limited).

In a variation, a user (such as an orthopedic surgeon), presented with a complex case in a particular patient, may submit the case for virtual consultation. The user may present the case virtually and may ask remote experts (e.g., those who may have more knowledge or education or training or experience) to opine about treatment approaches for the particular patient. The remote experts may choose to apply one or more approaches virtually, and submit them (including actions or inputs, video, audio, haptic, and/or metrics) for consideration by the user or by other remote experts. In this way, a patient may receive the benefit of consultation from local and remote experts.

Figure 3:
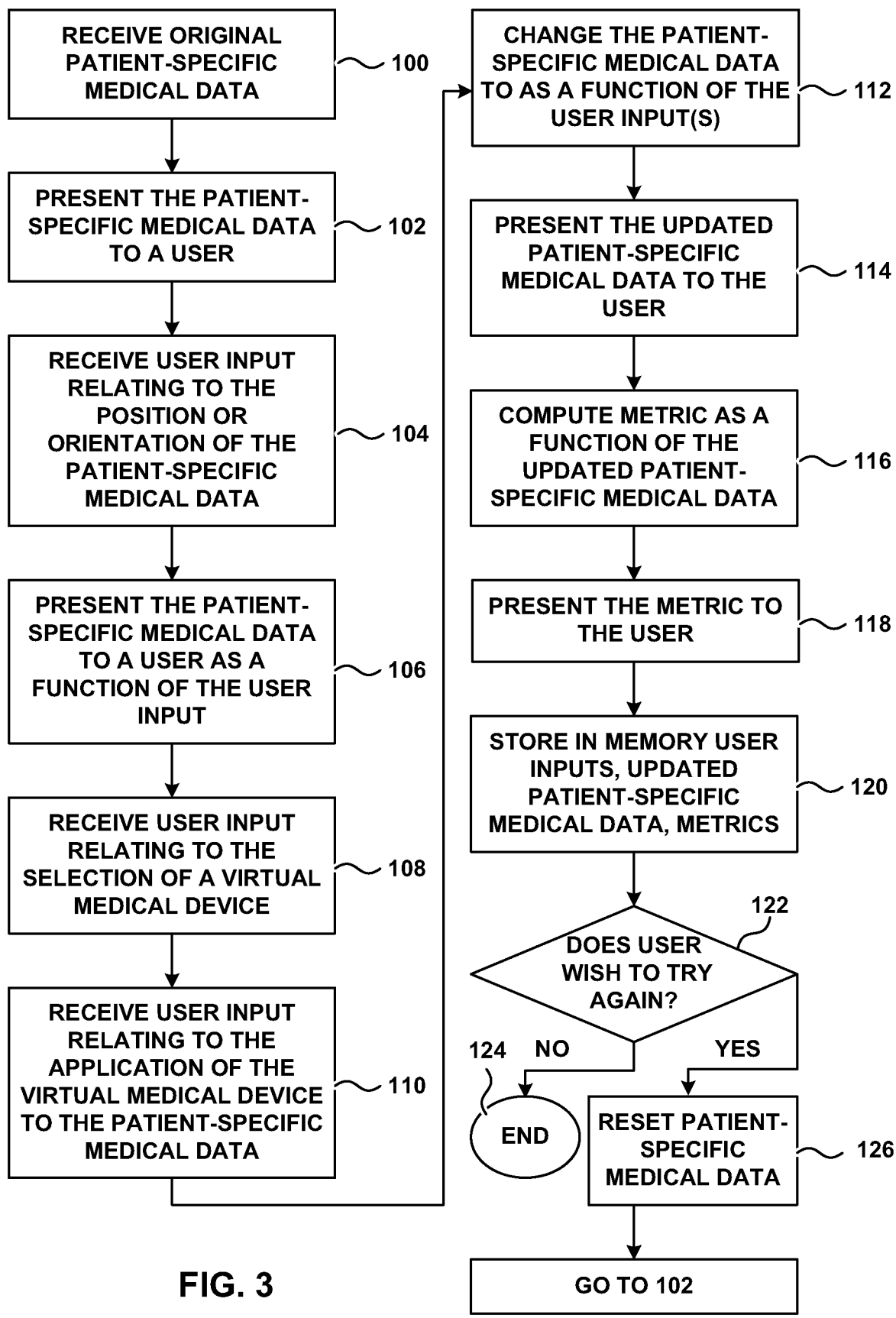
FIG. 3 is a flow diagram illustrating typical operations or steps carried out by a virtual reality platform or one or more components thereof.

FIG. 3 is a flow diagram illustrating a method that may be carried out by the apparatus described previously. A virtual reality platform 10 may receive patent-specific medical data (100) from any source, such as a CT scan or a magnetic resonance imaging (MRI) scan. This patent-specific data may be thought of as "original" patent-specific data in that it represents the condition of the virtual bone 58 before anything is done to the virtual bone 58 in the virtual environment. The patent-specific data may be stored in memory 16. The patient-specific data may presented to a user (102) by way of the virtual reality platform 10, such as by a three-dimensional image shown by headset 22, 52 of a disembodied virtual bone 58. The patient-specific data may presented in context with other information, such as virtual hands 60, 62. In a typical embodiment, the processor 14 and the headset 22, 52 may cooperate to present the data, with the headset 22, 52 presenting the data as a visual image of the patient's bone 58.

The user 50 may manipulate the virtual bone 58 through controllers 54, 56, thereby adjusting the apparent orientation of the virtual bone 58. The virtual reality platform 10 receives the user input (104) and, as a function of that input, presents the patient-specific information in a different orientation (106).

The user 50 may select a virtual medical device (which may be capable of virtual activation) and apply one or more treatment or repair operations to the virtual bone 58 through controllers 54, 56. The virtual reality platform 10 receives this user input (108, 110), and in response, may update (e.g., change, correct, modify) the patient-specific data from its original form, as a function of the user input (112). Such updates may reflect, for example, virtual cuts made in the virtual bone 58 with a virtual instrument 64, or the application to the virtual bone 58 of a virtual medical device such as a pin or brace, or the realignment of pieces of the virtual bone 58. The updated patient-specific data may be presented to the user 50 (114). As will be explained further below, updated patient-specific data typically is more than original patient data that has been reformatted, or rearranged, or reorganized, or otherwise presented in a different form; rather, updated patient-specific data typically reflects significant changes or transformations to the original patient-specific data, as a function not merely of processing but also as a function of user interaction.

The computer 12 may compute one or more metrics as a function of the updated patient-specific data (116). As discussed above, the metrics may be defined or computed in any of several ways. Generally, the metrics indicate the degree of success of was virtually done to the virtual bone 58; as previously discussed, typically a metric is generated as a result of a comparison of the virtual outcome to a metric standard. The virtual reality platform may display or otherwise present the metrics to the user 50 (118).

Information about what was done in the virtual environment—such as the original and updated conditions of the virtual bone 58, the inputs received from the user 50, the presentations that were presented as a function of those inputs, and generated metrics—may be stored in memory 16 (120).

An option may be presented to the user 50 to try again (122). If the user chooses not to try again, the simulation may be concluded (124). If the user 50 decides to try again, the patient-specific data may be reset to its original form (126) and re-presented to the user 50 (102).

One or more actions depicted in FIG. 3 may be repeated an arbitrary number of times. For example, there may be many user inputs received pertaining to the orientation of the virtual bone (106), and many presentations of the patient-specific data (108) as a function of the inputs. From the point of view of the user 50, the virtual bone 58 may appear to move with a fluid motion (rather than appear as a succession of different presentations of patient-specific data). Further, some actions shown in FIG. 3 are optional. Manipulation of the virtual bone (106, 108), for example, need not be performed in every case. Also, not all processes depicted in FIG. 3 need be performed in the order shown.

Figure 4:
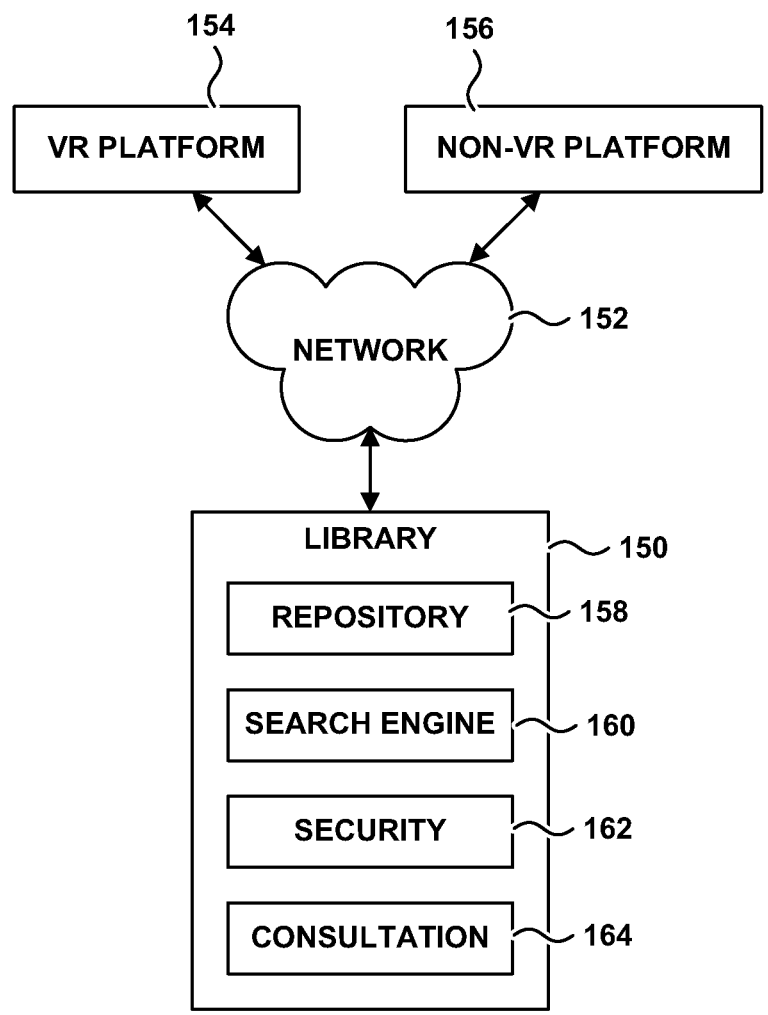
FIG. 4 is a block diagram illustrating sharing of knowledge obtained in part by virtual reality simulations.

FIG. 4 is a block diagram illustrating some ways in which knowledge obtained in part by virtual reality simulations may be shared. Information about virtual bones and virtual treatments of virtual bones may be stored in a library 150. The information in the library 150 may be accessed via a communication network 152, such as the Internet. Information may be contributed to the library by a virtual reality platform 154, such as the platform 10 shown in FIG. 1. Contributed information may include patient-specific information (as already noted, such patient-specific information may be scrubbed or encoded or otherwise handled to preserve patient confidentiality), virtual procedures performed, and metrics that were generated as a result. Contributed information need not pertain to a specific patient. A virtual reality platform 154 may also retrieve information from the library 150. It is contemplated that some information may be retrieved from the library 150 by a platform 156 (such as a computer system) that lacks virtual reality capability.

Within the library 150, the information may be stored in a repository 158, which may be searched with the aid of a search engine 160. A security module 160 may be employed to prevent unauthorized access to the information, or prevent unauthorized (and possibly spurious) contributions to the library 150, or protect of information that would ordinarily have a degree of confidentiality, or guard against corruption of the information by a malicious entity.

In a variation, a consultation module 164 may be implemented, in which a particular set of patient-specific data may be made available to authorized experts. The authorized experts may, for example, propose or advise as to various approaches for dealing with the challenges posed by the specific patient, or may warn against various risks. The authorized experts may also demonstrate techniques virtually, by applying those techniques virtually to the patient-specific data and generating metrics indicative of outcome. In this sense, the consultation module enables far greater interaction among experts than would a conventional consultation.

Figure 5:
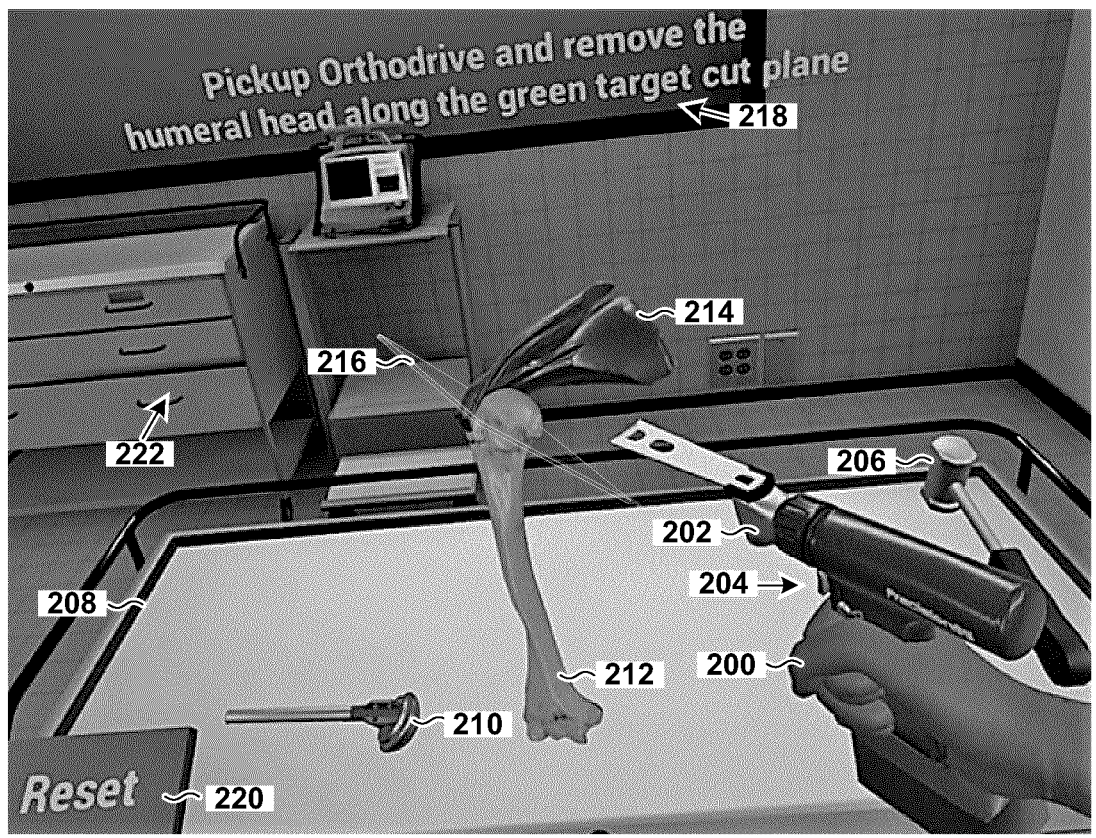
FIG. 5 is a screenshot of an illustrative virtual reality surgical system.

FIG. 5 is a screenshot, as may be seen by a user 50 by way of a headset such as way of the headset 52 shown in FIG. 2. FIG. 5 is in greyscale, but the images actually seen by the user 50 may be in colour. FIG. 5 is an image in two dimensions, but the images actually seen by the user 50 may be in three dimensions. FIG. 5 is a static image, but the images actually seen by the user 50 may seem to be in motion.

In FIG. 5, one virtual hand 200 is shown, in particular, the right hand. This virtual hand 200 (comparable to the virtual right hand 60 shown in FIG. 2) may correspond to and be directed by the right hand of the user 50, who may be equipped with a hand unit such as hand unit 56 shown in FIG. 2. In practice, a user may use two hand units and two virtual hands may be depicted.

The virtual hand 200 is holding a virtual medical device 202 (comparable to the virtual medical device 64 shown in FIG. 2). The hand unit held by the user may or may not bear a physical resemblance to the virtual medical device 202, and may or may not mimic the virtual medical device 202 in terms of weight or handling or tactile feedback. The virtual medical device 202 may include at least one virtual control 204, which when virtually operated may cause the virtual medical device 64 to become activated or deactivated in the simulation, or perform or in some particular fashion. The virtual control 204 may correspond to and be directed by the user who may operate one or more controls (such as a trigger or a button) on the hand unit. In general, the virtual medical device 202 typically behaves in the virtual world the same as, or close to, the way a real comparable medical device would behave in the real world. Operation of the virtual medical device 202 may generate tactile feedback (such as vibration or jolts or twisting) in the hand unit when the virtual medical device 202 interacts with something in the virtual world.

A second virtual medical device 206 is depicted as resting on a virtual table 208. In some implementations a user may lay the virtual medical device 202 onto the virtual table 208 and pick up the second virtual medical device 206. The second virtual medical device 206 is depicted as a hammer. The second virtual medical device 206 lacks controls, and may be a device that cannot be turned on or off; but the second virtual medical device 206 can be manipulated (e.g., swung or used to strike) to interact with another object in the virtual world.

Also depicted as resting on the virtual table 208 is a third virtual medical device 210. A user may virtually pick up the third virtual medical device 210 with the virtual hand 200 and manipulate the third virtual medical device 210. The third virtual medical device 210 is depicted as a medical implant, such as an artificial joint for a shoulder arthroplasty. The third virtual medical device 210 represents a device that may be implanted in or otherwise applied to a patient. The third virtual medical device 210 may be incapable of being virtually turned on or off, and may or may not include virtual moving parts. Other examples of such devices may be screws, braces, slings, casts, sutures, staples, birth control devices, artificial prosthetics/replacements, and so on.

A virtual bone 212 (comparable to the virtual bone 58 shown in FIG. 2) is depicted above the virtual table 208. The virtual bone 212 depicted in FIG. 5 is a humerus. The virtual bone 212 is depicted in concert with one or more virtual muscles 214 (such as rotator cuff muscles). In some cases, soft tissues other than or in addition to muscles may be depicted.

A user can visually distinguish the virtual bone 212 from the virtual muscles 214 by cues such as relative anatomical placement, texture, shading, and colour. Such cues may be present in the real world.

One or more visual elements not present in the real world, such as target cut plane 214, may also be depicted in the virtual world. Target cut plane 216 (comparable to the virtual frame 66 shown in FIG. 2) may serve as a guide for the user in performing a virtual procedure on a virtual bone. Even though the target cut plane 216 might not have a corresponding real world structure, the target cut plane 216 can show a user an approximate location and angle for a cut, in relation to anatomical features that can be seen in the real world.

FIG. 5 illustrates a typical scenario: the user is to use the first virtual medical device 202 to remove the head of the virtual humerus 212, without damaging the virtual muscles 214 or the attachment site on the greater tubercle of the virtual humerus 212. Removal of a humeral head in the real world may not be expected to be a gentle procedure; the procedure may require invasive or destructive actions such as cutting or grinding or drilling. The simulation depicted in FIG. 5 can virtually simulate some of the physical challenges of a real-world procedure. The target cut plane 216 identifies the location and angle and anatomical features that would be associated with a good removal of the virtual humeral head, with reduced chances of damaging other virtual anatomical structures. Following removal of the virtual humeral head, further procedures may be performed on the virtual humerus 212 to make the virtual humerus 212 ready to receive the virtual joint implant 210. Thereafter, the virtual joint implant 210 may be implanted.

Optional information 218 may include text instructions that guide the user as to what steps to take, how to take them, hazards to avoid or that may cause concern, and any other useful information (including information that need not direct a user what to do). The text of the information 218 may be in any language. In FIG. 5, the information 218 may seem to float in the air, or the information 218 may seem to be projected upon a virtual wall or a virtual display or a virtual blackboard, for example.

In FIG. 5, a virtual reset button 220 may be presented in any fashion. The user may control a hand unit, thereby controlling the virtual hand 200, to virtually depress or otherwise actuate the virtual reset button 220. Actuation of the virtual reset button 220 may cause the simulation to go back to the beginning, so that the user can try to perform the virtual procedure anew. Buttons other than a full reset (such as a virtual button skipping back one stage of a multi-stage virtual procedure, not shown in FIG. 5) may also be presented.

The virtual world may include one or more pieces of virtual equipment 222 that make the virtual world seem more interesting and more like the real world. Equipment such as a cabinet, a crash cart, a medical scope, a supply station, an electrical outlet, and the like, may be included in the virtual world. Features such as inclusion of a realistic virtual table 208 and realistic walls and floor may add to the realism of the virtual world. The virtual equipment 222 may be decorative or functional or a combination thereof. A virtual supply cabinet, for example, may be nothing more than a decorative virtual prop; or a virtual supply cabinet may be capable of being opened by the virtual hand 200, and the virtual contents thereof brought and used in the virtual world.

Figure 6:
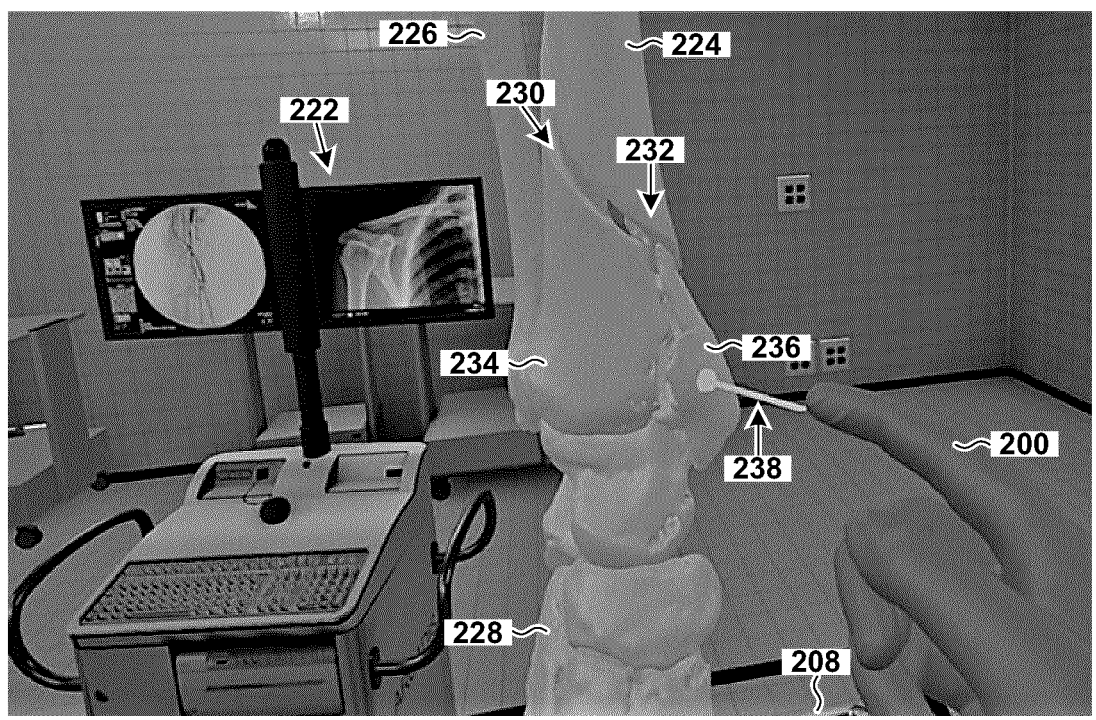
FIG. 6 is a second screenshot of an illustrative virtual reality surgical system.
Figure 7:
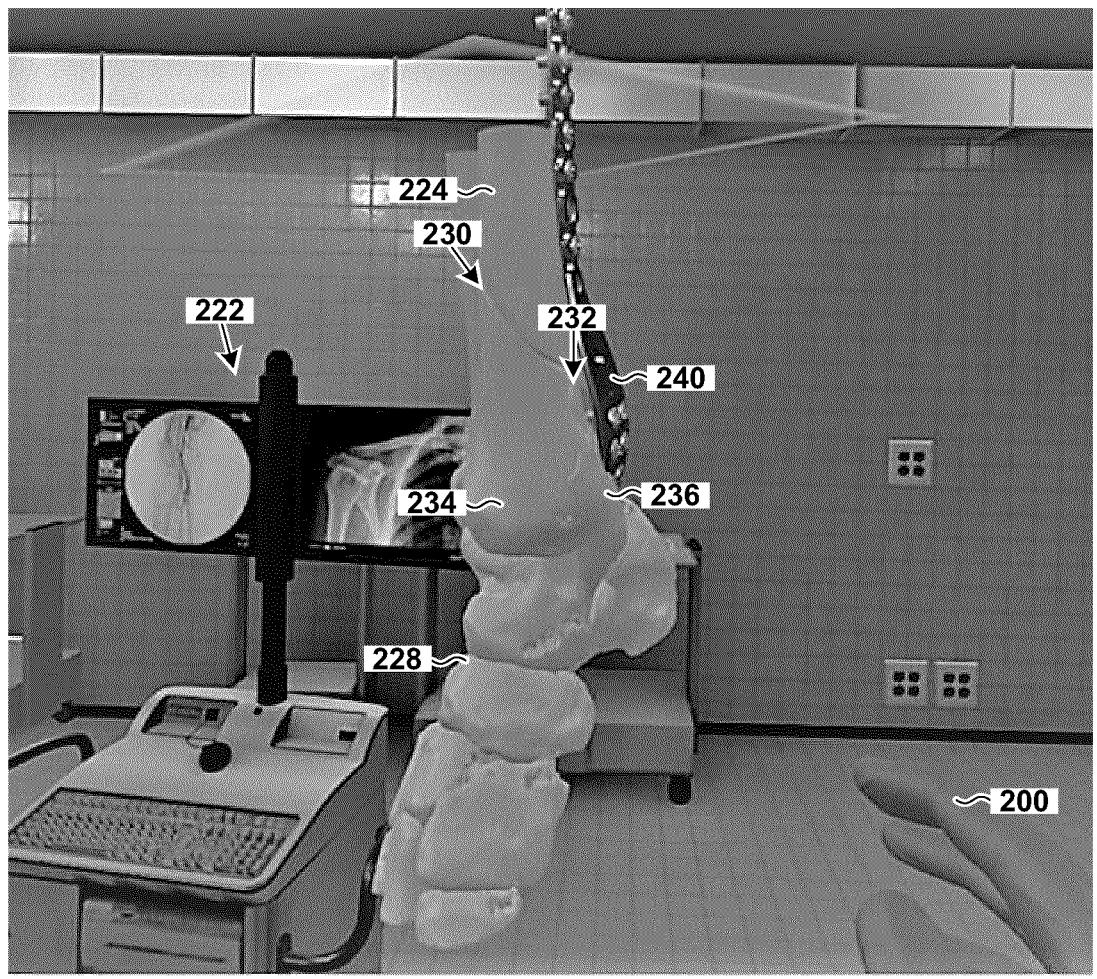
FIG. 7 is a third screenshot of an illustrative virtual reality surgical system.

FIG. 6 and FIG. 7 are screenshots illustrating manipulation of a virtual bone, or pieces of a virtual bone, in the virtual world. In FIGS. 6 and 7, the area of the virtual body affected is the foot, ankle and lower leg. (Note that in FIGS. 6 and 7, imaging equipment 222 depicts the shoulder region; in this illustration, the equipment 222 is not demonstrating functional aspects.)

FIG. 6 depicts a virtual tibia 224 and a virtual fibula 226, along with nearby virtual bones such as virtual tarsal bones 228. In FIG. 6, the virtual tibia 224 is exhibiting at least two distinct virtual fractures 230, 232. As a result of the virtual fractures 230, 232, there are two distinct virtual bone fragments 234, 236 distinguishable from the main body of the virtual tibia 224.

The virtual bones and fragments 224, 226, 228, 234, 236 depicted in FIG. 6 may be based upon actual patient-specific data taken from one or more imaging systems, such as a CT scan.

An actual real-world patient exhibiting fractures such as those depicted in FIG. 6 would be expected to develop disability and/or discomfort if the fractures were to be untreated. Medical experience has shown that such disability and discomfort can likely be reduced significantly by realigning, refitting, or otherwise returning the bone fragments back to their original locations and orientations with respect to the tibia. Procedures for achieving such results can sometimes be difficult; such a procedure may entail, for example, deciding which bone fragments ought to be repositioned, and in what order and in what manner, or deciding whether a medical device such as a brace ought to be applied, as well as the kind of medical device and the manner of application.

In FIG. 6, virtual bone fragments 234, 236 are, in the virtual world, independently movable with respect to the virtual tibia 224. In FIG. 6, the virtual hand 200 is moving virtual fragment 236. A visual indicator 238 may be used to show the user that the virtual fragment 236 is subject to the control of the virtual hand 200; the virtual hand 200 is in turn subject to the control of the user via a hand unit. By moving the hand unit, the user can seem to move the virtual fragment 236 relative to other virtual objects in the virtual world. The user may operate one or more controls on the hand unit to control or release control of the virtual hand 200 on the virtual fragment 236. The visual indicator 238 shown in FIG. 6 is a "beam" indicator that may not appear in the real world; the visual indicator 238 need not be presented in this fashion, however. Other forms of visual indicators may convey the same or similar information. In some instances, another indicator, such as audio indication or haptic feedback or illumination or color change, may indicate to a user whether a virtual fragment is under the control of a virtual hand. Any combination of indicators may be used, and in some circumstances it may be decided not to use any such indicators at all.

FIG. 7 depicts the virtual tibia 224 following repositioning of the virtual bone fragments 234, 236. As shown in FIG. 7, the virtual fractures 230, 232 exhibit much smaller gaps, and the virtual tibia 224 (with virtual bone fragments 234, 236) more closely resembles a normal tibia. An actual real-world patient exhibiting fractures such as those depicted in FIG. 7 would be expected to have an improved chance of healing with less disability and/or discomfort. A fourth virtual medical device 240, depicted as a brace, may be virtually positioned so as to help hold the virtual tibia 244 and virtual fragments 234, 236 in fixed relationships to one another. Virtual medical device 240 is depicted in FIG. 7 as engaging with virtual bones and fragments by way of screws (including some screws that may engage to a part of the virtual tibia that is not shown in the simulation).

The fourth virtual medical device 240 may be, for example, a representation of a brace that, in the real world, is contemporaneously available in various sizes and dimensions. In one variation of the concepts, the fourth virtual medical device 240 may be a brace that is representative of no contemporary brace in the real world. In other words, the virtual brace 240 may be shaped or adjusted or sized or otherwise created in the virtual world as a custom appliance for a particular patient, based upon that particular patient's actual patient data. The virtual medical device 240 may be made longer, for example, or wider, or more curved, or with fewer screw holes, or with screw holes at different sites. Techniques similar to those used by a user to manipulate virtual bones or virtual fragments can be used to customize the virtual brace 240, for example, by bending, shaping, enlarging or simplifying the virtual brace 240. Virtual marking, discussed below, can also aid in customization. Once the size, shape and dimensions of the virtual brace 240 are settled upon, the virtual brace can be realized (made to exist in the real world) by techniques such as three-dimensional printing or computer-controlled molding.

Figure 8:
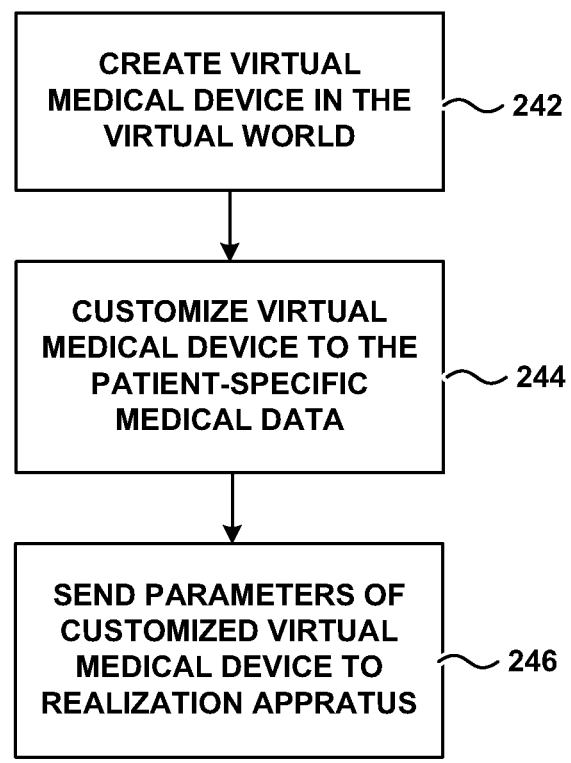
FIG. 8 is a flow diagram illustrating realizing a virtual medical device.

Comparable techniques can be applied for medical devices such as implants, prosthetics, and orthotics. An illustrative procedure for realizing a virtual medical device is shown in FIG. 8. The steps in this procedure would be carried out by the virtual reality or augmented reality surgical system, typically under the direction of a user. Upon instruction that a virtual medical device should be created in the virtual world, the system creates the virtual medical device (242). The virtual medical device may be created by, for example, retrieving a template virtual medical device from memory, or duplicating an existing virtual medical device, or combining a plurality of virtual medical devices. This virtual medical device need not be initially customized to the patient. Under the direction of the user, the system customizes the virtual medical device based upon the patient-specific data (244), resulting in a customized virtual medical device. When the user is satisfied that the customized virtual medical device is in a condition to be realized, the system sends parameters (such as dimensions, shape, materials, components) of the customized virtual medical device to a realization apparatus (246), which results in the customized virtual medical device becoming a customized, tangible medical device in the real world.

Returning once again to FIG. 7: Visual examination of the virtual bones shown in FIG. 7 suggests that the bone fragments have been successfully brought back to their original locations and orientations with respect to the tibia. The virtual procedure appears to be (in lay terms) a success. In some circumstances, however, the success or failure of a procedure (or the degree of success or failure) may be more difficult to assess. The system can assist with assessment through the employment of one or more metrics.

Figure 9:
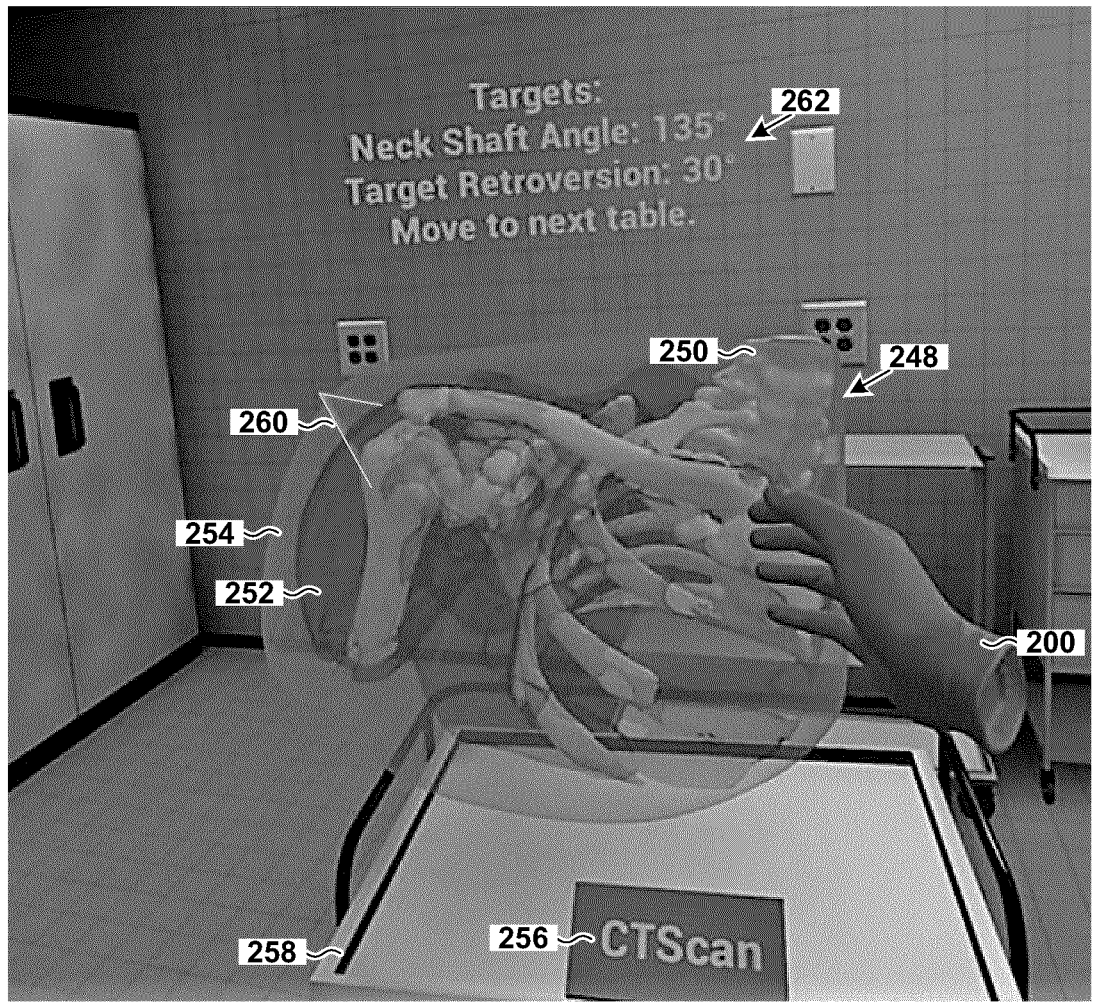
FIG. 9 is a fourth screenshot of an illustrative virtual reality surgical system.

FIG. 9 is an illustrative screenshot showing one potential feature of working with metrics. In FIG. 9, the area of the virtual patient in question is the shoulder. Displayed is an image 248 of the virtual shoulder area. Unlike the image displayed in FIG. 5, more than virtual bone and virtual muscle is displayed. The image 248 in FIG. 9 includes a virtual musculoskeletal structure, with virtual bones 250 (in addition to the virtual humerus), virtual muscles 252 (in addition to the virtual rotator muscles), and other virtual soft tissue 254. The image 248 may be based upon patient-specific data obtained from medical imaging apparatus. A source indicator 256 shows that the source of the patient-specific data is a CT scan. In some cases, a user may select patient-specific data from more than one medical imaging apparatus.

The image in FIG. 9 appears to hover over a virtual table 258. In this embodiment, the virtual table 258 may physically resemble the virtual table 208 described earlier, but the two virtual tables 208, 258 need not be the same virtual table, and there may be advantages to representing them as separate tables in the virtual world.

The purposes of virtual tables 208, 258 may be different. Virtual table 258 may be used for examining patient-specific data, but without changing the data. Virtual table 208 may be used for manipulating the patient-specific data. Separating the functions of virtual tables 208, 258 may simplify programming of the virtual reality system, but there may be other tangible benefits as well. Having two virtual tables 208, 258 may result in less confusion for a user. At virtual table 258, for example, it may be possible for the user, through use of a hand unit controlling virtual hand 200, to examine the patient-specific data from any desired viewpoint. The image 248 may be rotated this way and that, inverted, spun, magnified, or otherwise virtually moved about. Such freedoms may be more restricted at virtual table 208, at which the simulation is more closely related to treatment of a virtual patient. In the real world, a physician is unlikely to rotate or invert a patient in the same way in which a physician may rotate or invert a scrutinized X-ray, for example; having two virtual tables 208, 258 can help reinforce the understanding that there are differences between examining images of a patient and treating the patient.

FIG. 9 shows, in addition to virtual bones 250 and virtual muscles 252, and other virtual soft tissue 254, an optional reference or target plane 260. Target plane 260 may be, but need not be, the same as or similar to target cut plane 216 in FIG. 5. In FIG. 9, target plane 260 may be used to identify locations or angles of anatomical structures, for example, rather than locations or angles at which procedures are to be performed.

Written information 262 may identify data or instructions that may be useful in analysis of the image 248. Such information 262 may include, for example, anatomical data, or data about a pathology, or data about metrics, or instructions or recommendations for proceeding, or any combination thereof. In FIG. 9, the words, "Move to next table" may help reinforce the understanding that virtual table 258 is principally for examination of images, and virtual table 208 is for performance of procedures.

Figure 10:
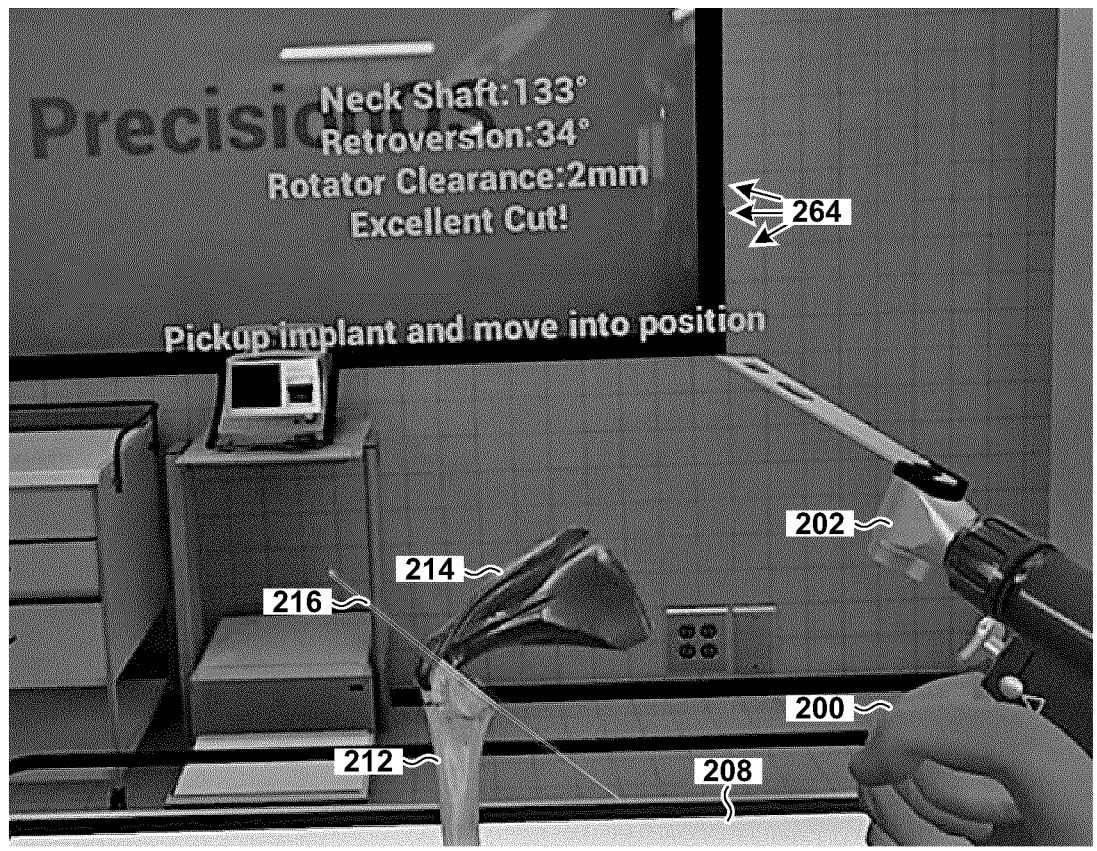
FIG. 10 is a fifth screenshot of an illustrative virtual reality surgical system.

FIG. 10 is an illustrative screenshot showing another potential feature of working with metrics. FIG. 10 is similar to FIG. 5, but FIGS. 5 and 10 represent different stages in a virtual procedure (such as a virtual shoulder arthroplasty). In FIG. 5, the information 218 identifies a short-term goal for the virtual procedure (removing the head of the virtual humerus 212). In FIG. 10, the virtual procedure has been performed, and the written post-procedure information 264 may help evaluate how well the goal was attained.

Some of the post-procedure information 264 may be metrics, which may include information evaluative of the virtual procedure. In FIG. 10, three particular considerations (neck shaft angle, retroversion angle and rotator clearance) are identified and quantified. Other pertinent considerations may be presented as well. In the example of FIG. 10, the actual virtual cut of the virtual humerus 212 was very close to the target plane 216. Further, the position of the virtual cut on the virtual humerus 212 was also satisfactory: information pertaining to retroversion and muscle clearance were quantified and indicated as being good. An optional shorthand notation—"Excellent Cut!"—summarizes how well the virtual procedure was performed. Further instructions pertaining to introduction of the virtual implant 210 (not shown in FIG. 10) are also presented. Such instructions reinforce the notion that the virtual procedure proceeded well enough to move to the next stage.

The metrics in the post-procedure information 264 may be supplied promptly upon completion of the virtual procedure. A user can assess in a brief time whether or not an approach applied in the virtual world would have a good chance of attaining a good result. The metrics may be computed and assessed according to techniques such as those identified previously.

Figure 11:
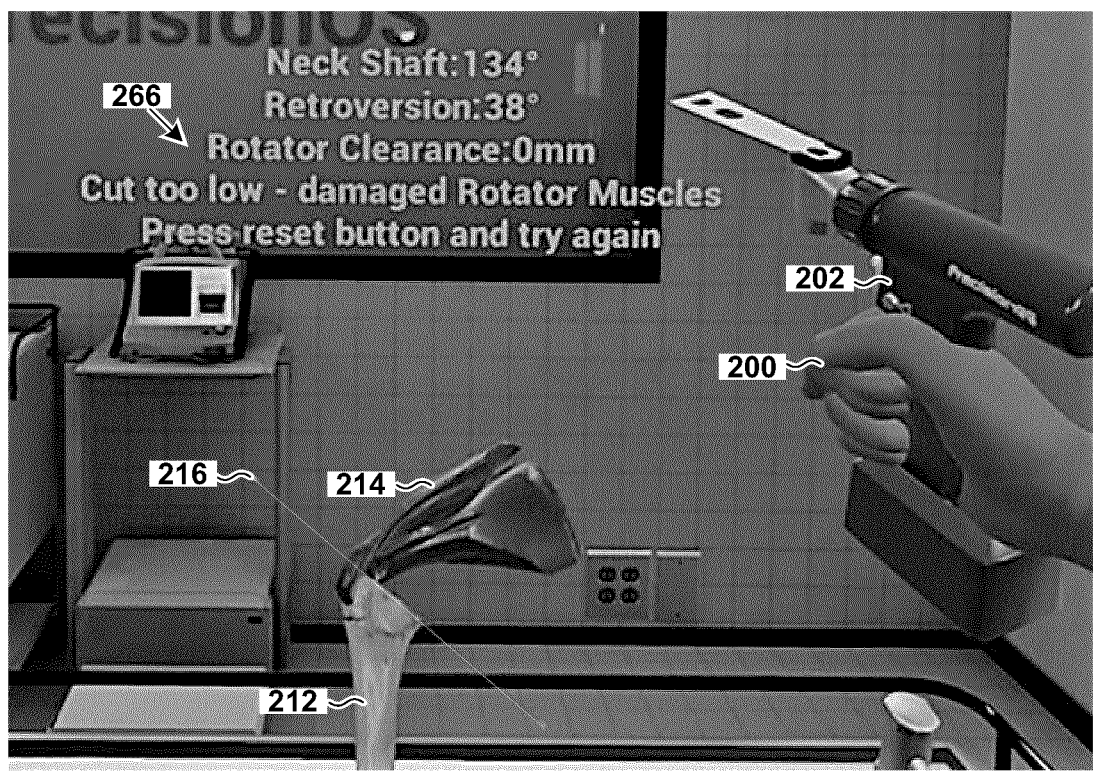
FIG. 11 is a sixth screenshot of an illustrative virtual reality surgical system.

FIG. 11 is an illustrative screenshot showing a further potential feature of working with metrics. In FIG. 11, the virtual procedure has been performed, and the written post-procedure information 266 indicate that the results were less than desirable. The metrics in the post-procedure information 266 may be a disappointment to the user, but they may be useful to the user should the user wish to try to perform the virtual procedure again. In FIG. 11, the metrics identify the angle of the cut as being close to a target angle, but the cut was positionally off-target on the virtual humerus 212 and the virtual muscles 214 were contacted by (and potentially damaged by) the virtual medical instrument 202. These metrics represent indications that the virtual procedure, as performed by the user, has significantly deviated from the standards deemed desirable (or perhaps essential) for the virtual patient, and that better results might be expected to be attainable (an assumption that, in the real world, may not be valid for a particular patient for any number of reasons). The information 266 includes instructions that the user ought to press the reset button 220 (not shown in FIG. 11) and make another attempt. If the user chooses to make another attempt, the user may be presented with a view similar to the screenshot shown in FIG. 5.

Figure 12:
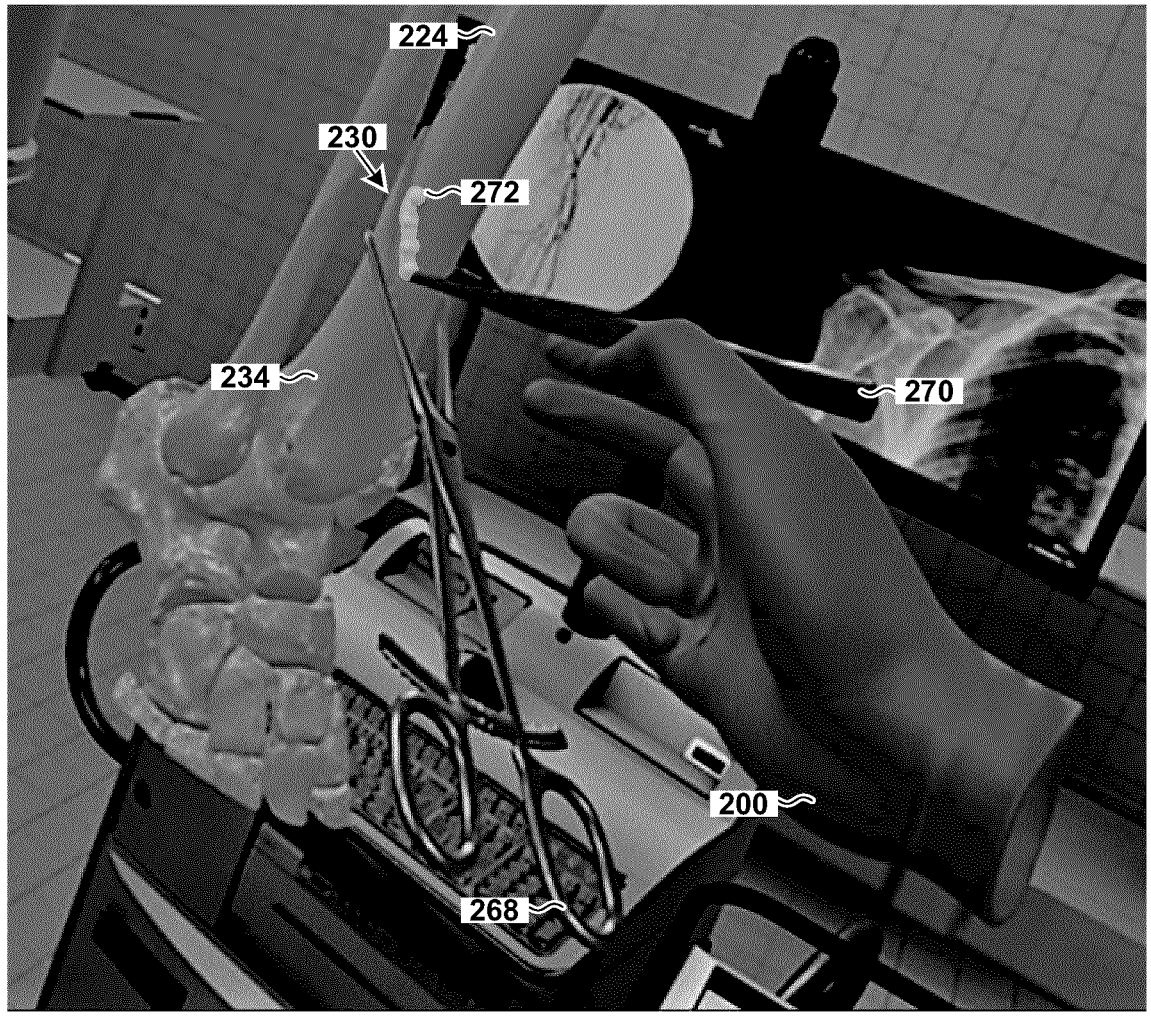
FIG. 12 is a seventh screenshot of an illustrative virtual reality surgical system.
Figure 13:
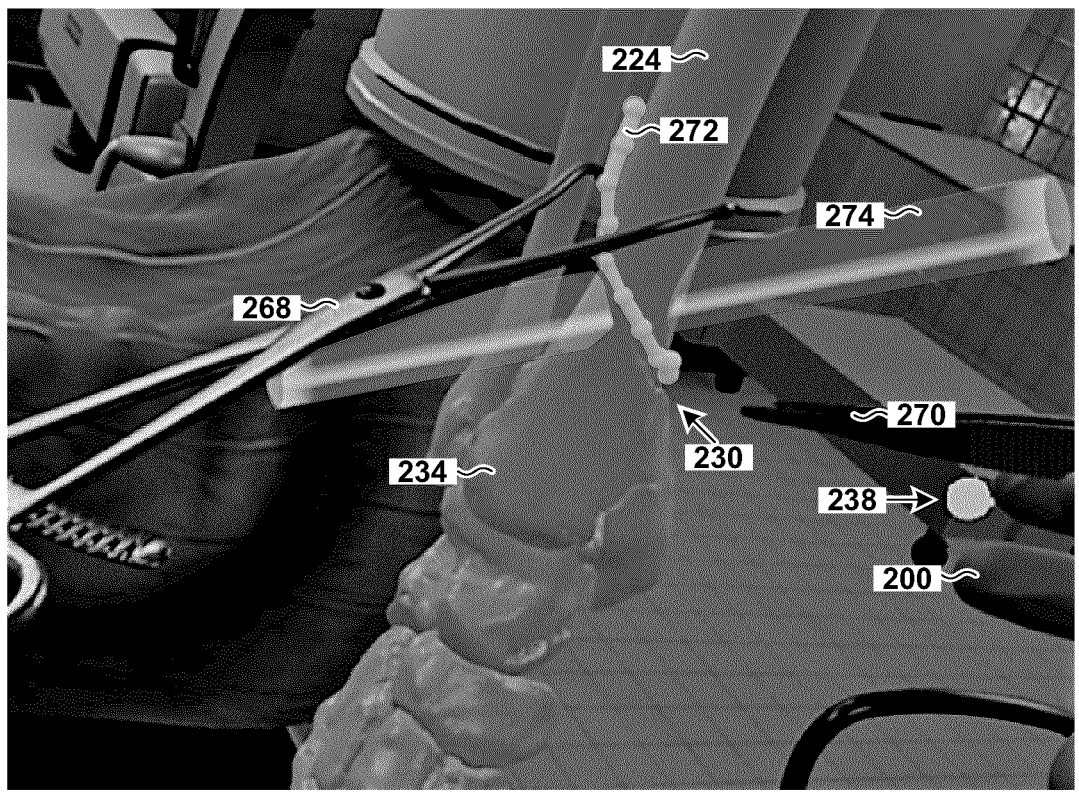
FIG. 13 is an eighth screenshot of an illustrative virtual reality surgical system.

FIG. 12 and FIG. 13 are illustrative screenshots showing one way in which metric standards may be created. In FIG. 12, a spiral leg fracture is depicted similar to FIG. 6 and FIG. 7. In FIG. 12, a virtual clamp-type forceps 268 is shown clamping the virtual tibia 224 and a virtual fragment 234. Such clamping may represent a temporary fixation in the virtual world, comparable to a procedure in the real world to temporarily hold the bones in a relatively fixed position, in preparation for a procedure that may hold the bones in an improved, longer-lasting relative position.

In the virtual world, identifying the contours of a fracture may be difficult for a machine to do (perhaps especially if the virtual bones are being held in temporarily fixed position). In order for a metric standard to be developed for performing a more longer-lasting procedure that will address the virtual fracture, the machine may benefit from or require confirmation from a user about the contours of the virtual fracture.

FIG. 12 illustrates one technique for depicting the contours of a virtual fracture. Such a process would likely not have a comparable process that would be performed in the real world, but may be performed in the virtual world to improve the simulation (and improve the virtual patient's chances).

In FIG. 12, the virtual hand 200 holds a fifth virtual medical device 270, embodied as a tweezer-type forceps. With the tweezer-type forceps 270, the virtual hand 200 has begun making a virtual fracture mark 272 proximate to the virtual fracture 230 (the virtual fracture 230 separating a virtual bone 224 from a virtual fragment 234). One way to define the virtual fracture mark 272 is for the virtual hand 200 (under the control of a user via a hand unit) to virtually touch sites along the virtual tibia 224 proximate to the virtual fracture 230. The simulation may mark each touch site with a dot, and connect successive dots with a line, as depicted in FIG. 12. Haptic feedback in the hand unit may supply the user with additional confirmation that a site on the virtual tibia 224 has been virtually "touched." As depicted in FIG. 12, the virtual fracture mark 272 need not extend the entire length of the virtual fracture 230, and the virtual fracture mark 272 need not match the virtual fracture 230 exactly. In FIG. 12, the virtual fracture mark 272 is close to the virtual fracture 230, but displaced slightly proximally (closer to centre of the body of the virtual patient). The virtual fracture mark 272 nevertheless may closely track the path of the virtual fracture 230.

Virtual marking such as is depicted in FIG. 12 may be used for purposes other than identifying virtual fractures. Virtual marking may be used to identify other virtual physical features in the virtual anatomy. Virtual marking may also be used to identify the contours, dimensions or other features (such as locations of virtual screw holes) of a virtual medical device as described with respect to FIG. 8.

FIG. 13 shows the virtual bones of FIG. 12 from a slightly different angle. The virtual clamp 268 is still in place. The user, via control of the virtual hand 200 and the virtual tweezer-type forceps 270, has virtually marked more sites than in FIG. 12, so the virtual fracture mark 272 is longer and more closely marking the virtual fracture 230. As a function of the virtual fracture mark 272, the simulation has generated a target cylinder 274, which may have no real world counterpart. The target cylinder 274 may have a size (such as a cross-sectional area, which need not be strictly circular), an angle (relative to any anatomical landmark or landmarks) and a location (relative to any anatomical landmark or landmarks). Using the virtual fracture mark 272, the cylinder 274 may be generated in any of several ways. For example, the cylinder 274 may be perpendicular (strictly perpendicular or substantially perpendicular) to the virtual fracture mark 272 (or perpendicular to a plane that is close to the virtual fracture mark 272), and thus perpendicular to the virtual fracture 230. Another possibility is that the target cylinder 274 may be generated at a site where the virtual bones or fragments 224 and 234 have a large area of contact.

If the virtual fracture 230 were to be repaired with a virtual screw, the target cylinder 274 may represent where and how the screw ought to be placed. In other words, the target cylinder 274 may represent the basis for a metric standard for evaluation of placement of a virtual screw (or other virtual medical device). The target cylinder 274 may include a standard error or buffer zone, such that placements in the buffer zone may generally result in generation of a similar metric. The target cylinder 274 need not be restricted to application to virtual screws, but may represent a target for manipulation or for any other operation with any other virtual medical device, such as a virtual clamp or a virtual orthopedic instrument.

During a virtual procedure, the target cylinder 274 may be visible in the virtual world to a user, or it may be invisible (just as target cut plane 216 in FIG. 5 may be displayed for a user or not). The metric for evaluating how well a virtual screw has been placed may be in relation to the location and angle of the target cylinder 274.

Explicit identification of fractures by a virtual fracture mark 272 is not the only way in which metric standards may be established. Even with fractures, other techniques for identifying targets and establishing metric standards may be employed. In some instances, for example, the simulation may automatically identify what appears to be a fracture, and invite the user to confirm or disagree or correct.

Figure 14:
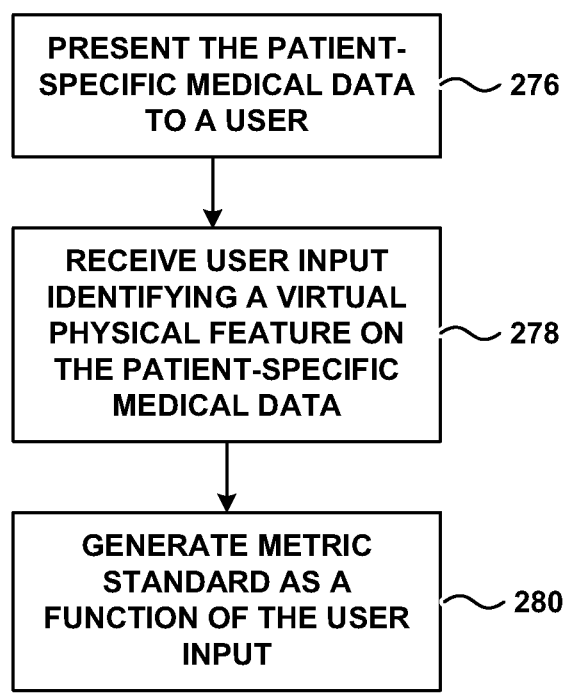
FIG. 14 is a flow diagram illustrating typical operations or steps carried out for user-assisted metric standard creation.

FIG. 14 is a flow diagram illustrating typical operations or steps carried out for user-assisted metric standard creation, such as has been illustrated with FIG. 12 and FIG. 13. A virtual reality platform 10 may present patent-specific medical data to a user (276). The presentation may be in the form of an image of the patent-specific medical data, such as is depicted in FIG. 12 and FIG. 13. The virtual reality platform 10 receives input from the user identifying a virtual physical feature on the patent-specific medical data (278). The virtual physical feature may be a virtual fracture such as is illustrated with FIG. 12 and FIG. 13, or some other virtual physical feature. The virtual physical feature may be, for example, a structure such as a virtual muscle or nerve or vessel that is to be avoided, or a fragile virtual structure to be treated with care, or a virtual injury that is not a fracture. The user input may comprise virtually marking a virtual structure such as is illustrated with FIG. 12 and FIG. 13, or it may comprise confirming virtual structures automatically identified by the virtual reality platform 10, for example.

The virtual reality platform 10 generates a metric standard as a function of the user input (280). As has been previously explained, a metric standard is criterion that can serve as a basis for comparison between the virtual outcome of a simulation and a good (if not excellent or ideal) outcome. A metric for the virtual outcome is computed as a function of the virtual outcome and the standard (or in some cases, more than one standard).

Although many prospective advantages of the concepts have been mentioned or described already, the concepts may realize one or more additional benefits.

A physician generally strives to do no harm. A simulation such as described herein, should it cause harm, would harm a simulated patient, rather than the actual patient. Further, the simulation enables the user to practice, try out and/or repeat various approaches for treating the patient (which may use patient-specific data), with the expectation (supported by many studies) that such simulations will reduce the risk of actual harm coming to the patient when a selected approach is actually applied to an actual patient.

A further potential advantage may be the potential for users to self-train, that is, to practice techniques, or learn new skills, or improve existing skills, or "brush up" their techniques, all without doing so on a living and breathing patient. In the course of self-training, the user may work on considerations of the user's own methods. For example, a user may be left-handed, but may wish to practice techniques in which the right hand is dominant or more active (or vice versa, for a right-handed user). This may result in improvement of valuable skills, in that some medical moves may be more easily performed right-handed, while others may be more easily performed left-handed. Similar to working on hand dominance, a user may work on the user's eye dominance or vision training, such that a user may approach a problem effectively from multiple angles or viewpoints.

The manipulation of data and instructions in a machine, and the operation upon virtual patient data in a virtual reality environment, do not make the concepts described here completely intangible. On the contrary, the description of the concepts herein includes numerous tangible effects. The presentation of data to a user—whether in the form of a virtual bone or a virtual instrument or a virtual hand or a metric or haptic feedback—is a real presentation, involving a tangible effects and changes in state of input-output elements 20. Indeed, an advantage of the concepts is that tangible effects (visual and/or auditory and/or haptic and/or evaluations) may be produced by one or more medical procedures without an actual patient being subjected to those procedures. The methods described herein are not bare algorithms but have been tied to one more machines. It may further be noted that the processes described herein do not involve mere automation of already-known processes, since the already-known processes do not include (for example) features such as computation of metrics or resetting a living patient's condition so that a physician may have another try for a potentially better result.

The embodiments described above and shown in the drawings are intended to be examples only. Alterations, modifications and variations can be effected to the particular embodiments without departing from the scope of the concept, which is defined by the claims appended hereto.

What is claimed is:

1. A virtual reality system, comprising:
   memory configured to receive and store original patient-specific medical data;
   a headset configured to present the original patient-specific medical data as a first three-dimensional visual image to a user;
   at least one hand unit comprising at least one sensor to receive first input from the user applying a virtual medical device to the original patient-specific medical data;
   a processor configured to receive the original patient-specific medical data, and to receive the first input, and to generate updated patient-specific medical data as a function of the original patient-specific medical data and the first input;
   wherein the headset is further configured to present the updated patient-specific medical data as a second three-dimensional visual image;
   wherein the processor is further configured to compute a metric as a function of the updated patient-specific medical data and a standard; and
   wherein the headset is further configured to present the metric to the user,
   wherein the original patient-specific medical data includes patient-specific data about a musculoskeletal structure of the patient,
   wherein the patient-specific data about a musculoskeletal structure of the patient includes patient-specific data about a bone of the patient, and the first three-dimensional visual image comprises a virtual bone, and
   wherein the first input is from the user applying the virtual medical device to perform a treatment or repair operation to the virtual bone.

2. The virtual reality system of claim 1, wherein the at least one hand unit is to receive second input from the user re-orienting the original patient-specific medical data, and wherein the headset is further configured to present a third three-dimensional visual image as a function of the original patient-specific medical data and the second input.

3. The virtual reality system of claim 1,
   wherein the at least one hand unit is a first hand unit, the virtual reality system further comprising a second hand unit comprising at least one sensor to receive second input from the user applying the virtual medical device to the original patient-specific medical data; and
   wherein the processor is further configured to receive the second input, and to generate updated the patient-specific medical data as a function of the second input.

4. The virtual reality system of claim 1,
   wherein the at least one hand unit is to receive third input from the user applying a virtual mark to the original patient-specific medical data; and
   wherein the processor is further configured to receive the third input, and to generate the standard as a function of the third input.

5. The virtual reality system of claim 1,
   wherein the at least one hand unit is to receive third input from the user applying a virtual mark to the original patient-specific medical data; and
   wherein the processor is further configured to receive the third input, and to generate parameters of a customized virtual medical device a function of the third input.

6. The virtual reality system of claim 1,
   wherein the processor is configured to generate a haptic output as a function of the original patient-specific medical data and the first input, and
   wherein the at least one hand unit further comprises a haptic feedback element to present the haptic output tactilely to the user.

7. The virtual reality system of claim 1, further comprising a three-dimensional printer communicative with the processor,
   wherein the virtual medical device comprises a brace, and
   wherein the processor is further configured to print the brace using the three-dimensional printer.

* * * * *

UNITED STATES PATENT AND TRADEMARK OFFICE
CERTIFICATE OF CORRECTION

| | |
|---|---|
| PATENT NO. | : 11,127,306 B2 |
| APPLICATION NO. | : 16/072490 |
| DATED | : September 21, 2021 |
| INVENTOR(S) | : Goel et al. |

It is certified that error appears in the above-identified patent and that said Letters Patent is hereby corrected as shown below:

In the Drawings

Figure 3, Box 112, Lines 2-3: "DATA TO AS A FUNCTION" should be --DATA AS A FUNCTION--.

In the Specification

Column 1,
Line 19, "apparatus involve manipulation" should be --apparatus involving manipulation--.

Column 2,
Line 31, "injuries diseases" should be --injuries, diseases--.

Column 3,
Line 43, "simulation may performed" should be --simulation may be performed--.

Column 4,
Line 56, "described in connection a" should be --described in connection with a--.
Line 60, "concepts may applied to more..." should be --concepts may be applied to more--.

Column 5,
Line 35, "but may also be the case" should be --but it may also be the case--.
Line 50, "spin" should be --spine--.
Line 62, "should and elbow" should be --shoulder and elbow--.

Column 6,
Line 7, "connecting tissue" should be --connective tissue--.
Line 23, "such a computerized" should be --such as computerized--.

Signed and Sealed this
Fifth Day of July, 2022

Katherine Kelly Vidal
*Director of the United States Patent and Trademark Office*

Column 8,
Line 1, "can assist in the user" should be --can assist the user--.

Column 9,
Line 50, "patent specific data" should be --patient specific data--.
Line 52, "patent specific data" should be --patient specific data--.
Line 53, "patent specific data" should be --patient specific data--.
Line 56, "patent specific data" should be --patient specific data--.
Line 57, "data may presented" should be --data may be presented--.
Line 60, "data may presented" should be --data may be presented--.

Column 11,
Line 13, "protect of information" should be --protect information--.
Line 29, "such as way of the headset 52" should be --such as by way of the headset 52--.
Line 52, "or perform or in some particular fashion." should be --or perform in some particular fashion--.

Column 18,
Line 32, "patent specific data" should be --patient specific data--.
Line 34, "patent specific data" should be --patient specific data--.
Line 37, "patent specific data" should be --patient specific data--.

Column 19,
Line 24, "a tangible effects" should be --tangible effects--.
Line 30, "one more machines." should be --one or more machines--.

In the Claims

Column 20,
Claim 3 (Line 31), "generate updated the patient-specific" should be --generate the updated patient-specific--.